(12) United States Patent  
Olson (10) Patent No.: US 8,376,960 B2  
(45) Date of Patent: Feb. 19, 2013

(54) MEDICAL DEVICES WITH VARIABLE STIFFNESS

(75) Inventor: Greg Olson, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1984 days.

(21) Appl. No.: 11/190,983

(22) Filed: Jul. 27, 2005

(65) Prior Publication Data

US 2007/0043306 A1     Feb. 22, 2007

(51) Int. Cl.  
*A61B 5/00*     (2006.01)

(52) U.S. Cl. .................................. 600/585; 604/95.04

(58) Field of Classification Search ................ 600/585; 604/95.04  
See application file for complete search history.

(56) References Cited

U.S. PATENT DOCUMENTS

| | | | |
|---|---|---|---|
| 5,800,421 A | | 9/1998 | Lemelson |
| 6,058,323 A | * | 5/2000 | Lemelson ............... 600/408 |
| 6,852,251 B2 | * | 2/2005 | Sheng et al. ............ 252/512 |
| 2003/0014021 A1 | * | 1/2003 | Holmen ................... 604/294 |
| 2004/0054322 A1 | | 3/2004 | Vargas |

FOREIGN PATENT DOCUMENTS

| | | |
|---|---|---|
| DE | 43 27 219 A1 | 2/1995 |
| EP | 0 455 362 A2 | 11/1991 |
| EP | 1 400 581 A1 | 3/2004 |

OTHER PUBLICATIONS

Makela, Kimmo. "Characterization and performance of electrorheological fluids based on pine oils" May 21, 1999.*  
T. Guarino et al., "The Effect of Solvent and Particle Dielectric Constants on the Electrorheological Properties of Water-Free ER Fluids," Electrorheological Fluids, Proceedings of the International Conference, Oct. 15-16, 1991, pp. 167-174.  
R. A. Anderson, "Effects of Finite Conductivity in Elelctrorheological Fluids," Electrorheological Fluids, Proceedings of the International Conference, Oct. 15-16, 1991, pp. 81-90.  
Thomas C. Halsey, "Electrorheological Fluids," *Science*, New Series, vol. 258, No. 5083 (Oct. 30, 1992), 761-766.  
Mustafa Yavuz et al., "ELectrorheological Properties of Suspensions Prepared from Polystyrene-*Block*—Polyisoprene Copolymer," *Turk J Chem*, 25 (2001), 19-32.  
Wing Yim Tam et al., "New Electrorheological Fluid: Theory and Experiment," *The American Physical Society*, Physical Review Letters, vol. 78, No. 15 (Apr. 14, 1997), 2987-2990.  
Weijia Wen et al., "The giant electrorheological effect in suspensions of nanoparticles," National Publishing Group, Nature Materials, vol. 2, (Nov. 2003), 727-730.  
M. Whittle et al., "The structure of smart fluids," *Nature*, vol. 358, (Jul. 30, 1992), 373.  
C. A. Randall et al., "High Dielectric Constant Particulate Materials for Electrorheological Fluids," Proceedings of the Fourth International Conference on Electrorheological Fluids, Jul. 20-23, 1993, Austria, pp. 60-66.

(Continued)

*Primary Examiner* — Max Hindenburg  
*Assistant Examiner* — Renee Danega  
(74) *Attorney, Agent, or Firm* — Seager, Tufte & Wickhem, LLC (57) ABSTRACT

Medical devices capable of having variable stiffness, and related methods, are disclosed. In some embodiments, a medical device includes an elongated member adapted to be inserted into a subject, and an electrorheological fluid carried by the elongated member.

30 Claims, 5 Drawing Sheets

OTHER PUBLICATIONS

C. A. Randall et al., "Dielectrophoretic Assembly: A Novel Concept in Advanced Composite Fabrication," Proceedings of the Fourth International Conference on Electrorheological Fluids, Jul. 20-23, 1993, Austria, pp. 516-525.

R. Liang et al., "Some New Evidence on Elctro-Rheological Mechanisms," Proceedings of the Fourth International Conference on Electrorheological Fluids, Jul. 20-23, 1003, Austria, pp. 233-250.

Yavuz, M., "Electrorheological Properties of Suspensions Prepared from Polystyrene-*Block*-Polyisoprene Copolymer," Turkish Journal of Chemistry, vol. 25, 2001, pp. 19-32.

Wen et al., "The giant electrorheological effect in suspensions of nanoparticles," Nature Materials, vol. 2, Nov. 2003, pp. 727-730.

International Search Report received in PCT Application No. PCT/US2006/028491, mailed Nov. 28, 2006.

* cited by examiner

MEDICAL DEVICES WITH VARIABLE STIFFNESS

TECHNICAL FIELD

The invention relates to medical devices, such as, for example, catheters, guide wires, and medical tubing.

BACKGROUND

Intravascular medical devices such as, for example, guidewires, catheters, and medical tubing, allow physicians to perform a medical procedure. As an example, a balloon catheter can be used to administer a variety of treatments. In an angioplasty procedure, the balloon catheter can be used to widen a constricted bodily vessel, such as a coronary artery. The balloon catheter can also be used to deliver a tubular member, such as a stent, that is placed in the body to reinforce or to reopen a blocked vessel.

In angioplasty, a balloon can be used to treat a stenosis, or a narrowing of the bodily vessel, by collapsing the balloon and delivering it to a region of the vessel that has been narrowed to such a degree that blood flow is restricted. The balloon catheter is passed over an emplaced guidewire that is inserted into a patient's vascular system at a convenient site, and subsequently delivered, e.g., pushed, through the vascular system to a target site. Upon reaching the site, the balloon is then expanded, e.g., by injecting a fluid into the interior of the balloon. Expanding the balloon can expand the stenosis radially so that the vessel can permit an acceptable rate of blood flow. After use, the balloon is collapsed and withdrawn.

In stent delivery, a stent is compacted on the balloon and transported to a target site. Upon reaching the site, the balloon can be expanded to deform and to fix the stent at a predetermined position, e.g., in contact with the vessel wall. The balloon can then be collapsed and withdrawn.

In some cases, the path that the device takes through the vascular system to the target site can be relatively tortuous, for example, requiring the device to change direction frequently. It is desirable for the medical device to have relatively good trackability so that it can travel along the tortuous path. At the same time, the device preferably has good pushability so that forces applied at the proximal end of the device can be transmitted distally to deliver the device.

SUMMARY

The invention relates to medical devices having selectively variable stiffness.

In one aspect, the invention features a medical device, including an elongated member adapted to be inserted into a subject, and an electrorheological fluid carried by the elongated member.

The electrorheological fluid is capable of providing the medical device with adaptable stiffness. By application of an electric field, the electrorheological fluid is capable of reversibly transitioning between a liquid-like state and a gel-like or solid-like state, thereby changing its stiffness and the stiffness of the medical device in which the electrorheological fluid is used. At a proximal portion, for example, the electrorheological fluid can enhance the pushability of the medical device, and a distal portion, the electrorheological fluid can enhance the flexibility and trackability of the device. The stiffness of the electrorheological fluid can be controlled by controlling the application of the electric field.

In another aspect, the invention features a medical device, including an elongated member adapted to be inserted into a subject, and an electrorheological fluid carried by the elongated member.

Embodiments may include one or more of the following features. The electrorheological fluid includes particles in a liquid. The particles include a composite having at least two different compositions. The particles include a first composition, and a second composition coating the first composition. The particles include a material selected from the group consisting of urea, butyramide, and acetamide. The liquid includes an oil. The elongated member includes a lumen, and the electrorheological fluid is in the lumen. The electrorheological fluid is on an exterior surface of the elongated member. The device is configured to apply an electric field to the electrorheological fluid. The elongated member includes two conductive members, the electrorheological fluid being between the two conductive members. The device includes a first portion having a first volumetric concentration of the electrorheological fluid, and a second portion having a second volumetric concentration of the electrorheological fluid different than the first volumetric concentration. The device includes a first portion having a first electrorheological fluid, and a second portion having a second electrorheological fluid different than the first electrorheological fluid. The device is catheter, such as a balloon catheter or a stent delivery catheter. The device is guidewire. The device includes multiple, independently-addressable portions of electrorheological fluid. The electrorheological fluid is contained in a receptacle.

In another aspect, the invention features a method, including providing a medical device having an elongated member and an electrorheological fluid carried by the elongated member, applying an electric field to the electrorheological fluid, and changing the rheological properties of the electrorheological fluid.

Embodiments may include one or more of the following features. The electric field is applied between two conductive members. The method includes applying different electric fields to the electrorheological fluid. The method includes applying a first electric field to a first electrorheological fluid, and applying a second electric field different from the first electric field to a second electrorheological fluid. The first and second electrorheological fluids have the different compositions. The first and second electrorheological fluids have different volumetric concentrations relative to the elongated member. The electrorheological fluid includes particles in a liquid. The particles include a composite having at least two different compositions. The particles include a first composition, and a second composition coating the first composition. The elongated member includes a lumen, and the electrorheological fluid is in the lumen. The electrorheological fluid is on an exterior surface of the elongated member. The medical device is tube, a balloon catheter, a stent delivery catheter, or a guidewire.

In another aspect, the invention features a method of selectively changing the stiffness of one or more predetermined portions of a medical device. The method includes applying an electric field to the medical device.

Other aspects, features and advantages will be apparent from the description of the preferred embodiments thereof and from the claims.

DETAILED DESCRIPTION

Figure 1A:
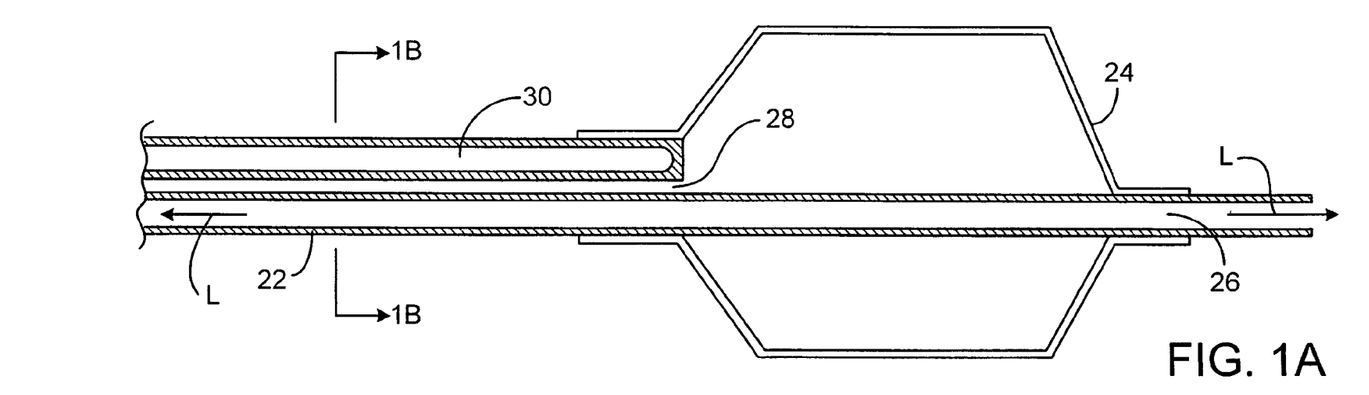
FIG. 1A is a cross-sectional view of an embodiment of an over-the-wire balloon catheter.
Figure 1B:
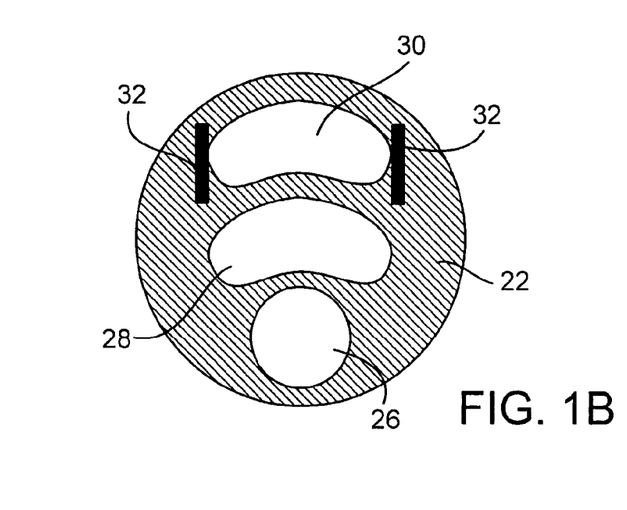
FIG. 1B is a cross section of the balloon catheter of FIG. 1A, taken long line 1B-1B.

Referring to FIGS. 1A and 1B, an over-the-wire balloon catheter 20 capable of having variable stiffness is shown. Balloon catheter 20 includes an elongated shaft 22 constructed to be inserted into a subject's vasculature (e.g., a bodily vessel), and an inflatable balloon 24 carried by the shaft at the distal end of the shaft. Shaft 22 includes three lumens extending along its length: a guidewire lumen 26, an inflation lumen 28, and a stiffening lumen 30. Guidewire lumen 26 is used to pass balloon catheter 20 over an emplaced guidewire (not shown), and to deliver the balloon catheter to a targeted site. Inflation lumen 28, which is in fluid communication with the interior of balloon 24, is used to inflate and to deflate the balloon with a fluid. Stiffening lumen 30 contains an electrorheological fluid that is capable of changing its resistance to flow to provide balloon catheter 20 with variable stiffness. As shown in FIG. 1B, balloon catheter 20 further includes two conductive members 32 that are constructed and arranged to apply an electric field to the electrorheological fluid in stiffening lumen 30.

The electrorheological fluid is a material whose rheological properties can be selectively varied, such as through application of an external electric field by conductive members 32. For example, under the application of an external field, the electrorheological fluid is capable of increasing its viscosity by transforming from a liquid-like material to a gel-like or solid-like material capable of exhibiting solid-like behavior, such as the ability to transmit shear stress. When the applied external field is removed, the electrorheological fluid is capable of quickly (e.g., less than 10 msec) and reversibly transforming from the gel-like or solid-like material to the liquid-like material. Thus, by integrating the electrorheological fluid with balloon catheter 20 and controlling the electric field that is applied, the stiffness of the balloon catheter can be controlled. When an electric field is applied, the electrorheological fluid transforms to the gel-like or solid-like material and increases the stiffness of balloon catheter 20; and when the electric field is removed, the electrorheological fluid transforms to the liquid-like material and decreases the stiffness of the balloon catheter, thereby increasing the flexibility of the balloon catheter.

In some embodiments, the electrorheological fluid includes a mixture, such as a colloidal suspension, of particles and a liquid that can exhibit high yield strength. On application of an electric field, induced polarization causes the particles to form elongated chains, columns, or fibrous structures aligned parallel to the electric field. An example of a particle is a composite particle having a barium titanyl oxalate core coated with a promoter such as urea, butyramide, acetamide, or acrylamide. The particles can have an average size of about 50-70 nm, and each particle can have a surface coating of about 3-10 nm. The particles can be present in a volume concentration of about 5% to about 50%. The liquid in the electrorheological fluid can be an electrically insulating, hydrophobic liquid, such as an oil, for example, silicone oils, mineral oils, engine oils, and hydrocarbon oils.

In some embodiments, the electrorheological fluid can be made as follows. The particles can be made by dissolving barium chloride in distilled water at 50-70° C. Separately, oxalic acid can be dissolved in water at 65° C. in an ultrasonic tank, with titanium tetrachloride slowly added. The two solutions can then be mixed in an ultrasonic bath at 65° C. Amorphous, nanometer-sized barium titanyl oxalate particles can be formed at this stage. Adding urea (a promoter) to the mixed solution can form a white colloid, which can be cooled to room temperature. The precipitate can be washed with water, filtered, and dried to remove trace water. The dried white powder can consist of nanoparticles coated with urea (BaTiO$(C_2O_4)_2$+$NH_2CONH_2$). The electrorheological fluid can be prepared by mixing the powder with, for example, silicone oil, and homogenizing the mixture in a high-speed grinding mill for about two hours. The mixture can then be vacuum dried at 105-120° C. for 1-3 hours. Other methods of the making electrorheological fluids are described in Sheng et al., U.S. Pat. No. 6,852,251; and Wen et al., "The Giant Electrorheological Effect in Suspensions of Nanoparticles" *Nature Materials*, Vol. 2, November 2003, 727-730, both hereby incorporated by reference.

Other embodiments of electrorheological fluids can be used. For example, other compositions for particles include ceramics such as silica or other glasses, alumina, titanium oxide, bismuth titanate, barium titanate (such as $Ba_4Ti_3O_{12}$ or $BaTiO_3$), strontium titanate, or lead magnesium niobate, as described in Randall et al., in *Electrorheological Fluids* (eds Tao, R. & Roy, G. D.) 60-66 (World Scientific, Singapore, 1994). In some embodiments, the particles can have more than one coating, such as a double coat including a conducting inner layer and an insulating, high dielectric constant outer layer. As an example, commercially available solid glass spheres (1.5-50 microns diameter) can be coated with an inner nickel layer (e.g., about 10 nm thick by electroless plating), and an outer titanium oxide coating (e.g., 10-60 nm thick by a sol-gel process). To avoid particle coagulation, an excess sugar solution can be used to form a buffer that is subsequently removed by heating. After heating (e.g., at 500° C. for ten hours) to remove organic components, the coated particles can be dispersed in a liquid, such as silicone oil. Doubly coated particles are described, for example, in Tam et al., *Phys. Rev. Let.* Vol. 78, Number 15, 14 Apr. 1997, p. 2987-2990. Other electrorheological fluids may include a block copolymer, such as those described in Yavuz et al., *Turk. J. Chem.* 25 (2001) 19-32.

Still referring to FIGS. 1A and 1B, conductive members 32 are configured to apply an electric field to the electrorheological fluid in lumen 30. As shown, conductive members 32 are parallel plates that extend for the substantial length of shaft 22 and parallel to the longitudinal axis (L) of balloon catheter 20. As a result, when conductive members 32 apply a field to an electrorheological fluid containing particles, the particles align into columns oriented transversely (e.g., perpendicularly) to longitudinal axis L. In other embodiments, conductive members 32 extend only at selected portion(s) of shaft 22. Balloon catheter 20 can include multiple, longitudinally-spaced pairs of conductive members 78 to which selected (e.g., different) electric fields can be applied to provide variable stiffness. Conductive members 32 can be configured to apply a DC electric field up to about 6,000 V/mm, e.g., about 1,000 V/mm to about 3,000 V/mm, and/or an AC electric field with a frequency of less than about 1,000 Hz. The conductive members can be connected to a generator by wires (not shown) that extend from the conductive members, proximally within shaft 22, and to the generator.

In other embodiments, the conductive members can be constructed and arranged to apply a field generally parallel to longitudinal axis L. For example, referring to FIG. 2, balloon catheter 40 includes multiple (as shown, three) stiffening cavities 42a, 42b, and 42c containing electrorheological fluid, and multiple pairs of conductive members 44a, 44b, and 44c configured to apply an electric field to their respective stiffening cavities. Each pair of conductive members 44a, 44b, and 44c includes two parallel plates arranged to apply an electric field parallel to longitudinal axis L, and as a result, particles in the electrorheological fluid can align parallel to the longitudinal axis L. Each pair of conductive members 44a, 44b, and 44c can be independently and selectively controllable to provide variable stiffness along the length of balloon catheter 40.

Figure 2:
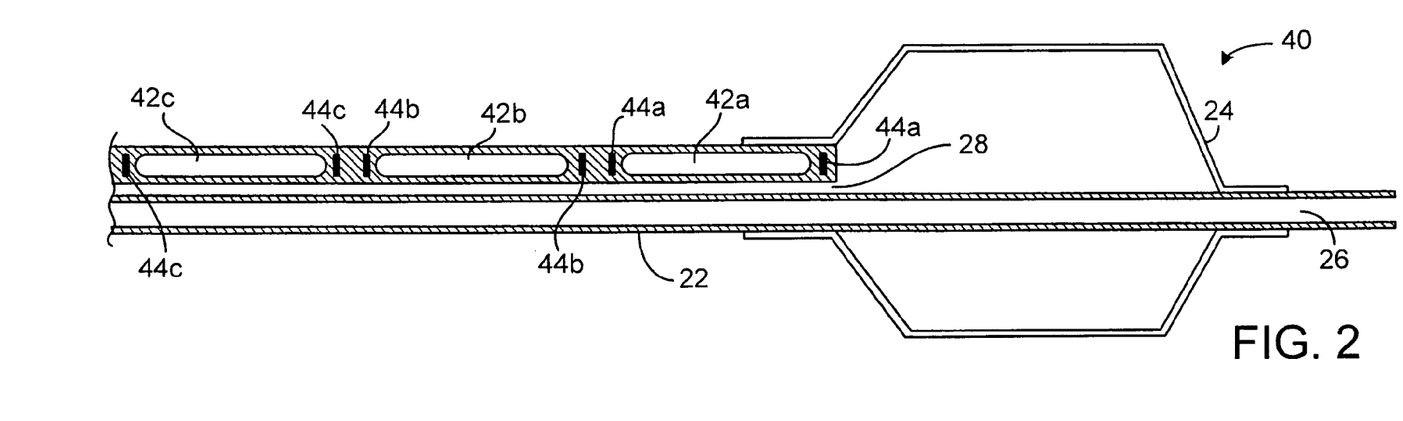
FIG. 2 is a cross-sectional view of an embodiment of an over-the-wire balloon catheter.

For example, during use, different electric fields can be applied to conductive members 44a, 44b, and 44c to provide different stiffness. At the distal portion of balloon catheter 40, a first, relatively low field or no field can be applied to conductive members 44a. As a result, the electrorheological fluid in stiffening cavity 42a does not align very much and the distal portion of the balloon catheter is relatively flexible, thereby allowing the balloon catheter to track a tortuous vasculature. At the more proximal portion of balloon catheter 40, a second, relatively high field (e.g., higher than the first field) can be applied to conductive members 44c. As a result, the electrorheological fluid in stiffening cavity 42c align relatively more than in cavity 42a, and the more proximal portion of the balloon catheter is relatively stiff. This stiffness allows balloon catheter 40 to be pushed through the vasculature. A third electric field between the first and second fields can be applied to conductive members 44b to provide an intermediate stiffness or a gradual change in stiffness, which can reduce buckling or kinking of balloon catheter. The fields applied to conductive members 44a, 44b, and 44c can be varied during use to provide the desired stiffness of balloon catheter 40. For example, after balloon catheter 40 has reached the targeted site, the field applied to distal conductive members 44a can be increased to make the distal portion stiffer, thereby helping balloon 24 to remain in position.

Balloon catheter 40 and 44 can be delivered, used and withdrawn according to conventional methods.

While a number of embodiments have been described, the invention is not so limited.

Figure 3:
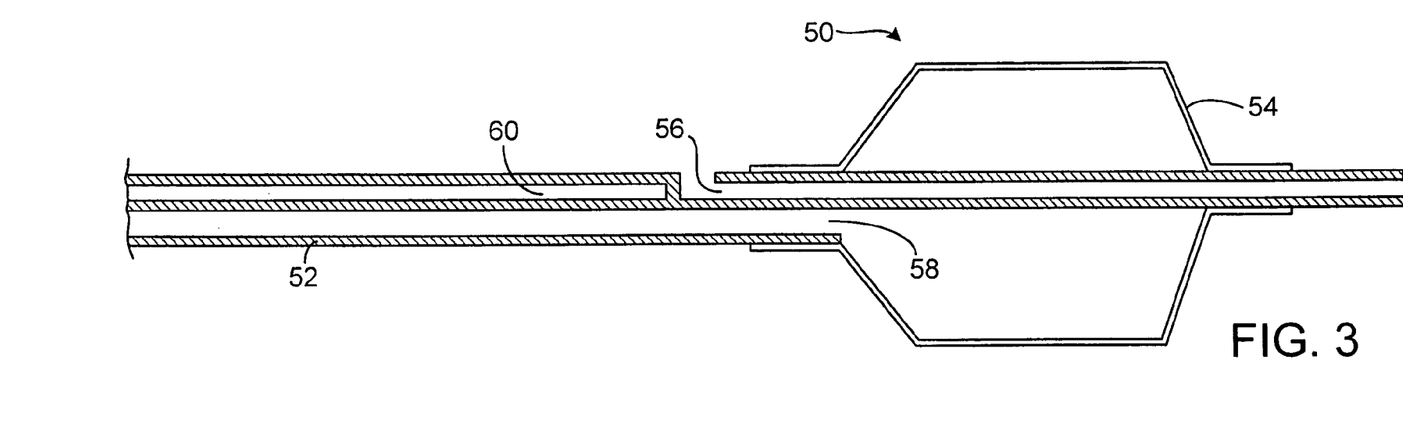
FIG. 3 is a cross-sectional view of an embodiment of a rapid-exchange balloon catheter.

As an example, an electrorheological fluid can be used in a rapid exchange or single operator exchange balloon catheter. Referring to FIG. 3, a rapid exchange balloon catheter 50 includes an elongated shaft 52 carrying an inflatable balloon 54. Shaft 52 includes a guide wire lumen 56, an inflation lumen 58, and a stiffening lumen 60 containing an electrorheological fluid. Balloon catheter 50 can include any of the embodiments of electrorheological fluid, stiffening lumens and cavities, and conductive members described herein.

Figure 4A:
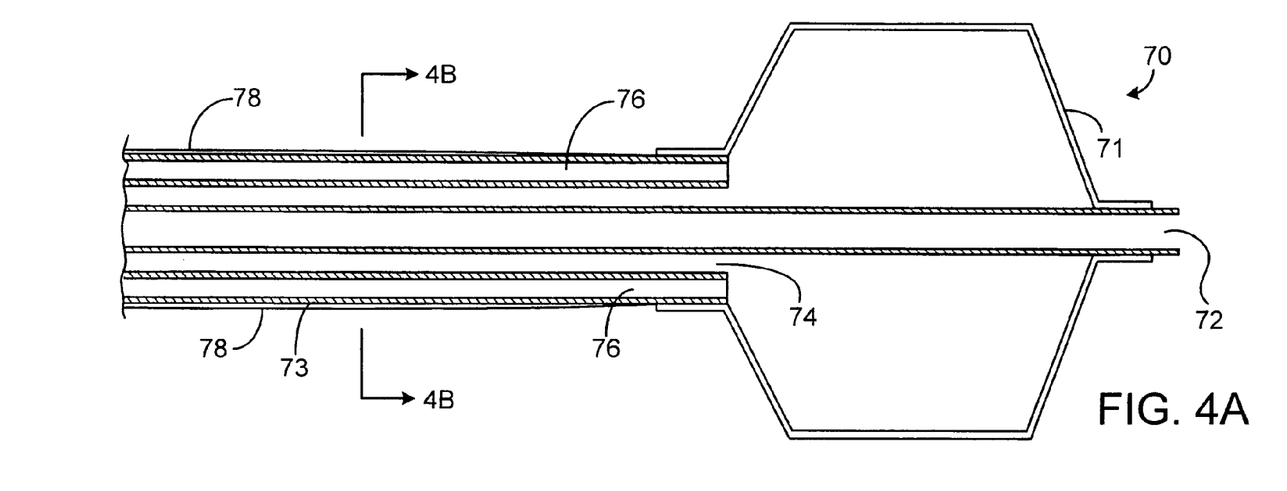
FIG. 4A is a cross-sectional view of an embodiment of an over-the-wire balloon catheter.
Figure 4B:
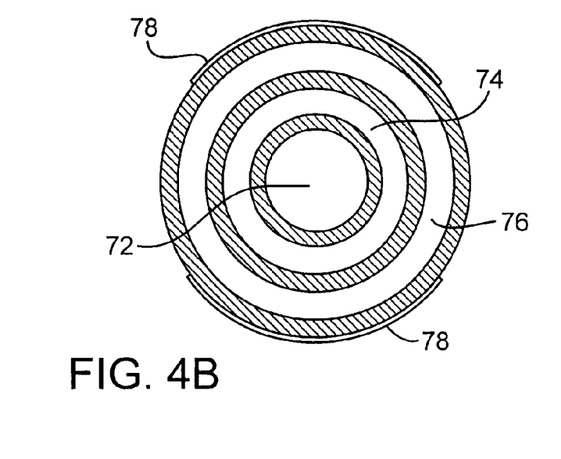
FIG. 4B is a cross section of the balloon catheter of FIG. 4A, taken along line 4B-4B.

FIGS. 4A and 4B show a balloon catheter 70 having a balloon 71 and a shaft 73 including a guide wire lumen 72, an inflation lumen 74, and a stiffening lumen 76 arranged in a coaxial relationship. Stiffening lumen 76 contains an electrorheological fluid. As shown, balloon catheter 70 further includes opposing conductive members 78 constructed and arranged to apply an electric field to the electrorheological fluid in stiffening lumen 76. As in catheter 20, conductive members 78 can extend the entire length of shaft 73 or only selected portion(s) of the shaft. Balloon catheter 70 can include multiple, spaced pairs of conductive members 78 to which selected (e.g., different) electric fields can be applied to provide variable stiffness. Conductive members 78 can be applied to shaft 73 using, for example, sputtering techniques.

Figures 5, 6:
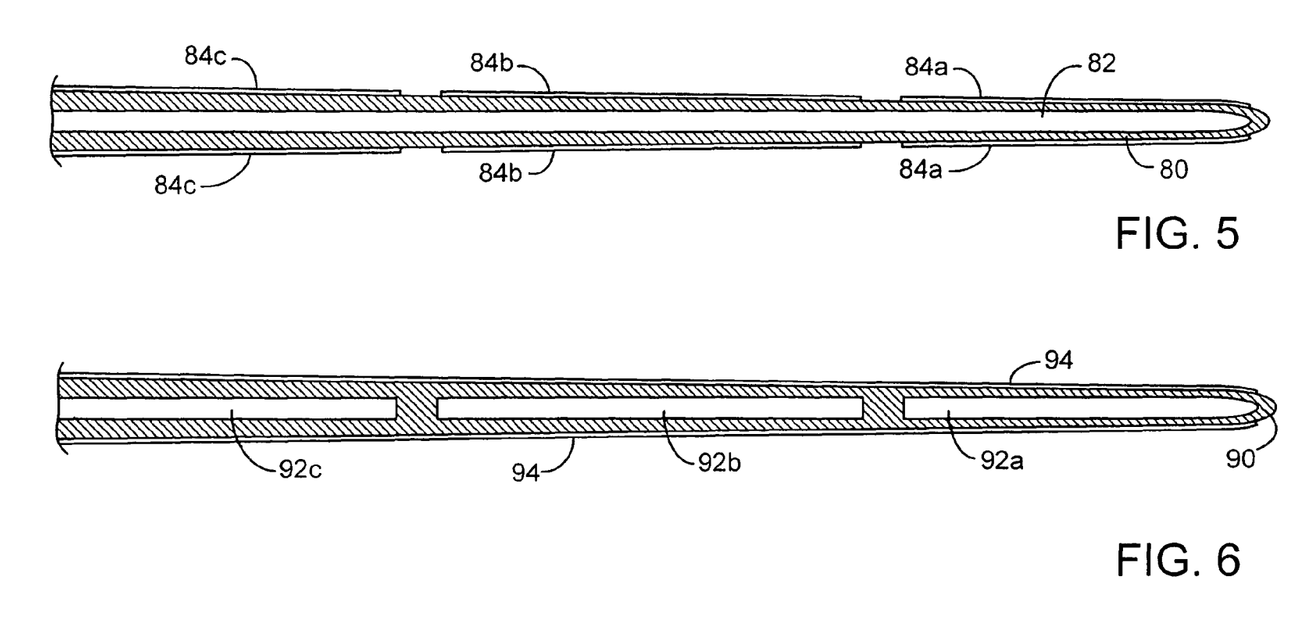
FIG. 5 is a cross-sectional view of an embodiment of a guidewire.
FIG. 6 is a cross-sectional view of an embodiment of a guidewire.

The electrorheological fluids described herein can also be applied to medical devices other than balloon catheters, such as guide wires. FIG. 5 shows a guide wire 80 having a stiffening cavity 82 containing an electrorheological fluid, and multiple (as shown, three) pairs of conductive members 84a, 84b, and 84c constructed and arranged to apply an electric field to the electrorheological fluid. Different electric fields can be independently applied to conductive members 84a, 84b, and 84c to effect variable stiffness along the length of guide wire 80. Alternatively or additionally, referring to FIG. 6, a guide wire 90 can include multiple (as shown, three) stiffening cavities 92a, 92b, and 92c containing electrorheological fluids, and conductive members 94 constructed and arranged to apply an electric field to the electrorheological fluid. Stiffening cavities 92a, 92b, and 92c may include the same composition of electrorheological fluid or different compositions of electrorheological fluids to effect differing stiffness. For example, for a given applied field, the electrorheological fluids in the proximal stiffening cavity(ies) may align more than the electrorheological fluids in the more distal stiffening cavity(ies), thereby making the proximal portions of the guide wire more stiff than the distal portions of the guide wire. Alternatively or additionally, stiffening cavities 92a, 92b, and 92c may have different concentrations of electrorheological fluids (e.g., particles) to effect variable stiffness. The proximal stiffening cavity(ies) may include a higher concentration of electrorheological fluid than the distal stiffening cavity(ies), thereby making the proximal portions more stiff than the distal portions. In other embodiments, guide wire 90 includes multiple (e.g., three) pairs of independently addressable conductive members constructed and arranged to apply electric fields to the multiple stiffening cavities 92a, 92b, and 92c. Having multiple pairs of conductive members provides greater control of the stiffness of the guidewire.

Figure 7:
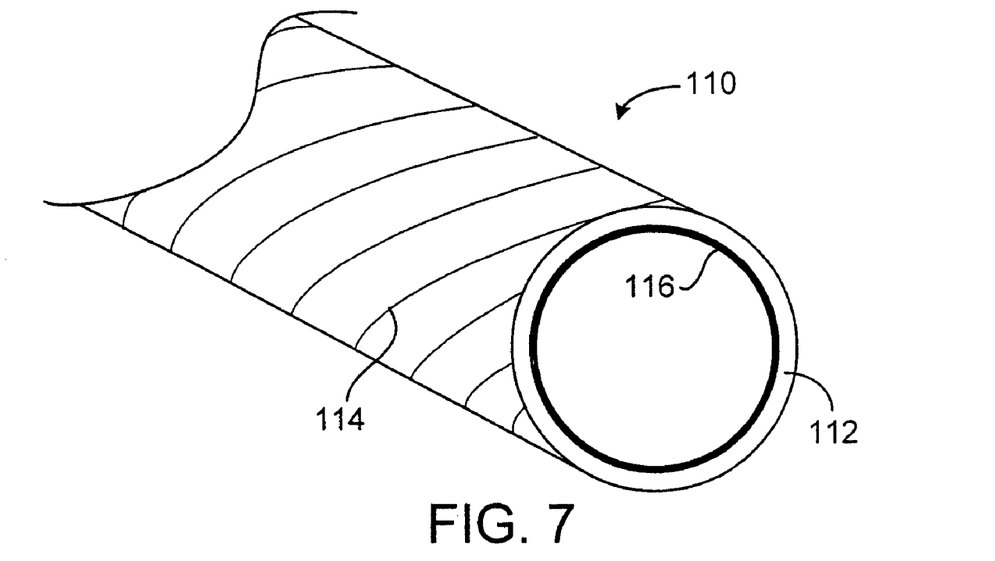
FIG. 7 is a cross-sectional and perspective view of an embodiment of an elongated member.

Other medical devices to which an electrorheological fluid can be applied include an inner tubular member and/or an outer sheath of a self-expanding stent delivery system, an elongated shaft of an endoscope, and other catheters, such as micro-catheters used to treat aneurysms. These devices can have an elongated member (for example, a tubular member) with a stiffening lumen or cavity, for example, as shown in FIG. 4B, and conductive members on the outer surface of the elongated member. In other embodiments, referring to FIG. 7, a medical device includes an elongated member 110 having a stiffening lumen or cavity 112 between two conductive members 114 and 116 that are disposed on the exterior and interior surfaces of the elongated member, respectively. Multiple, independently addressable conductive members can be formed on these surfaces, for example, as shown FIG. 5 and discussed herein.

Figure 8:
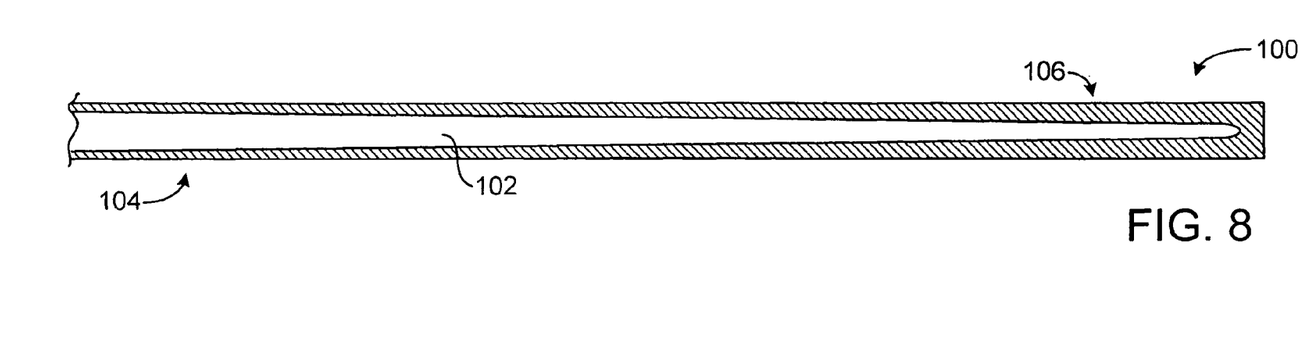
FIG. 8 is a cross-sectional view of an embodiment of a guidewire.

Variable stiffness can also be achieved by varying the size of the stiffening lumen or cavity. As an example, FIG. 8 shows a guide wire 100 having a stiffening cavity 102 with variable diameter containing an electrorheological fluid. As shown, the proximal portion 104 of guide wire 100 has a larger diameter than the distal portion 106 of the guide wire, and thus, the proximal portion contains a higher concentration of electrorheological fluid than the distal portion. Depending on the stiffness of the material from which guide wire 100 is made relative to the stiffness of the electrorheological fluid under an applied electric field, application of an electric field can make the proximal portion stiffer than the distal portion because more electrorheological fluid is aligned at the proximal portion.

The conductive members described herein need not be parallel plates, but can be, for example, two opposing curved members, for example, as shown in FIG. 4B.

One or more stiffening lumens or cavities of a medical device can include more than one compositions of electrorheological fluids.

Figure 9:
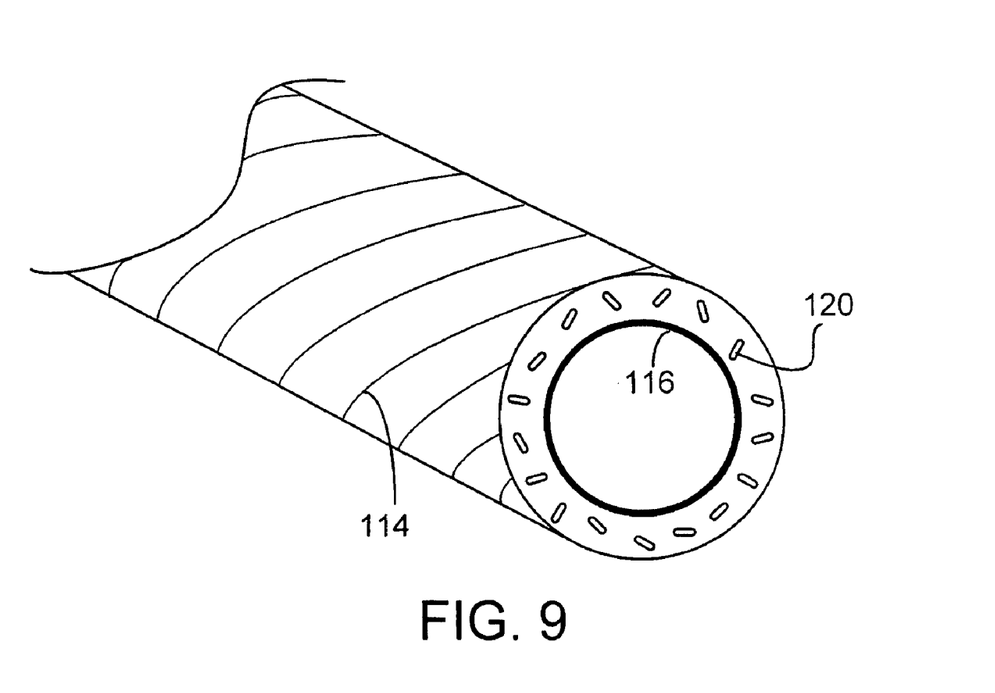
FIG. 9 is a cross-sectional and perspective view of an embodiment of an elongated member.

Other methods of carrying the electrorheological fluid on an elongated member can be used besides using a lumen or a cavity. For example, referring to FIG. 9, the electrorheological fluid(s) can be contained in receptacles 120 (such as thin-walled, flexible and sealed fibers) that are mixed (e.g., compounded) with the material (e.g., polymer) of the medical device or elongated member. Receptacles 120 can be made of polymers such as polypropylene, polyethylene, polysulfonate, Nylon, polyethyleneterephthalate (PET), or polyacetonitrile. Receptacles for containing a fluid are described in commonly-assigned U.S. Ser. No. 10/390,202, filed Mar. 17, 2003.

All publications, applications, and patents referred to in this application are herein incorporated by reference to the same extent as if each individual reference was specifically and individually indicated to be incorporated by reference in its entirety.

Other embodiments are within the claims.

What is claimed is:

1. A medical device, comprising:
    an elongated member adapted to be inserted into a subject; and
    an electrorheological fluid carried by the elongated member comprising a first portion having a first electrorheological fluid, and a second portion having a second electrorheological fluid different than the first electrorheological fluid.

2. The device of claim 1, wherein the electrorheological fluid comprises particles in a liquid.

3. The device of claim 2, wherein the particles comprise a composite having at least two different compositions.

4. The device of claim 3, wherein the particles comprise a first composition, and a second composition coating the first composition.

5. The device of claim 2, wherein the liquid comprises an oil.

6. The device of claim 2, wherein the particles comprise a material selected from the group consisting of urea, butyramide, and acetamide.

7. The device of claim 1, wherein the elongated member comprises a lumen, and the electrorheological fluid is in the lumen.

8. The device of claim 1, wherein the electrorheological fluid is on an exterior surface of the elongated member.

9. The device of claim 1, wherein the device is configured to apply an electric field to the electrorheological fluid.

10. The device of claim 9, wherein the elongated member comprises two conductive members, the electrorheological fluid being between the two conductive members.

11. The device of claim 1, wherein the first portion has a first volumetric concentration of the electrorheological fluid, and the second portion has a second volumetric concentration of the electrorheological fluid different than the first volumetric concentration.

12. The device of claim 1, wherein the device is catheter.

13. The device of claim 12, wherein the device is a balloon catheter or a stent delivery catheter.

14. The device of claim 1, wherein the device is guidewire.

15. The device of claim 1, comprising multiple, independently-addressable portions of electrorheological fluid.

16. The device of claim 1, wherein the electrorheological fluid is contained in a receptacle.

17. A method, comprising:
    providing a medical device comprising an elongated member and an electrorheological fluid carried by the elongated member;
    applying different electric fields to the electrorheological fluid, wherein the electric fields differ in intensity; and
    changing the rheological properties of the electrorheological fluid.

18. The method of claim 17, wherein the electric field is applied between two conductive members.

19. The method of claim 17, comprising applying a first electric field to a first electrorheological fluid, and applying a second electric field different from the first electric field to a second electrorheological fluid.

20. The method of claim 19, wherein the first and second electrorheological fluids have the different compositions.

21. The method of claim 19, wherein the first and second electrorheological fluids have different volumetric concentrations relative to the elongated member.

22. The method of claim 19 wherein the first electric field and the second electric field differ in intensity.

23. The method of claim 22 further comprising applying a third electric field to a third electrorheological fluid wherein the third electric field has an intensity between those of the first electric field and the second electric field.

24. The method of claim 17, wherein the electrorheological fluid comprises particles in a liquid.

25. The method of claim 17, wherein the particles comprise a composite having at least two different compositions.

26. The method of claim 17, wherein the particles comprise a first composition, and a second composition coating the first composition.

27. The method of claim 17, wherein the elongated member comprises a lumen, and the electrorheological fluid is in the lumen.

28. The method of claim 17, wherein the electrorheological fluid is on an exterior surface of the elongated member.

29. The method of claim 17, wherein the medical device is tube, a balloon catheter, a stent delivery catheter, or a guidewire.

30. The method of claim 17 wherein the step of applying different electric fields to the electrorheological fluid comprises applying a first electric field to a first portion of electrorheological fluid, maintain the first electric field at a first intensity for a period of time and subsequently increasing the intensity of the first electric field.

* * * * *